(12) United States Patent
Niwa et al.

(10) Patent No.: US 6,277,940 B1
(45) Date of Patent: Aug. 21, 2001

(54) MATERIAL FOR A SOFT INTRAOCULAR LENS

(75) Inventors: Kazuharu Niwa; Tatsuya Ojio; Toru Kawaguchi, all of Kasugai (JP)

(73) Assignee: Menicon Co. Ltd, Nagoya (JP)

( * ) Notice: Subject to any disclaimer, the term of this patent is extended or adjusted under 35 U.S.C. 154(b) by 0 days.

(21) Appl. No.: 09/248,265

(22) Filed: Feb. 11, 1999

(51) Int. Cl.$^7$ .................. C08F 220/26; C08F 220/30; A61L 27/00

(52) U.S. Cl. .................. 526/328.5; 526/261; 526/310; 526/312; 526/320; 526/329.7; 526/328

(58) Field of Search ................. 526/328, 328.5, 526/329.7, 320, 310, 261, 312

(56) References Cited

U.S. PATENT DOCUMENTS

| | | | |
|---|---|---|---|
| 4,528,311 | * 7/1985 | Beard | 524/91 |
| 5,662,707 | * 9/1997 | Jinkerson | 623/6 |
| 5,814,680 | * 9/1998 | Imafuku | 523/106 |
| 5,891,931 | * 4/1999 | Leboeuf | 522/64 |
| 6,015,511 | * 1/2000 | Yasuda | 264/1.7 |

FOREIGN PATENT DOCUMENTS

| | | |
|---|---|---|
| 0898972 | 3/1999 | (EP) . |
| 9640303 | 12/1996 | (WO) . |

\* cited by examiner

*Primary Examiner*—Fred Zitomer
(74) *Attorney, Agent, or Firm*—Browdy and Neimark

(57) ABSTRACT

There is provided a material for a soft intraocular lens, which has excellent transparency and flexibility, can be inserted from a small incision and has an high refractive index independent on a water content. The material comprises (A) 5–25 % by weight of acrylate containing an aromatic ring, (B) 50–90 % by weight of 2-hydroxyethyl (meth)acrylate, and (C) 5–45 % by weight of a (meth) acrylate monomer having the coefficient of water absorption of the homopolymer thereof of not more than 30 % by weight, except for (A) acrylate containing an aromatic ring and (B) 2-hydroxyethyl (meth)acrylate.

6 Claims, 1 Drawing Sheet

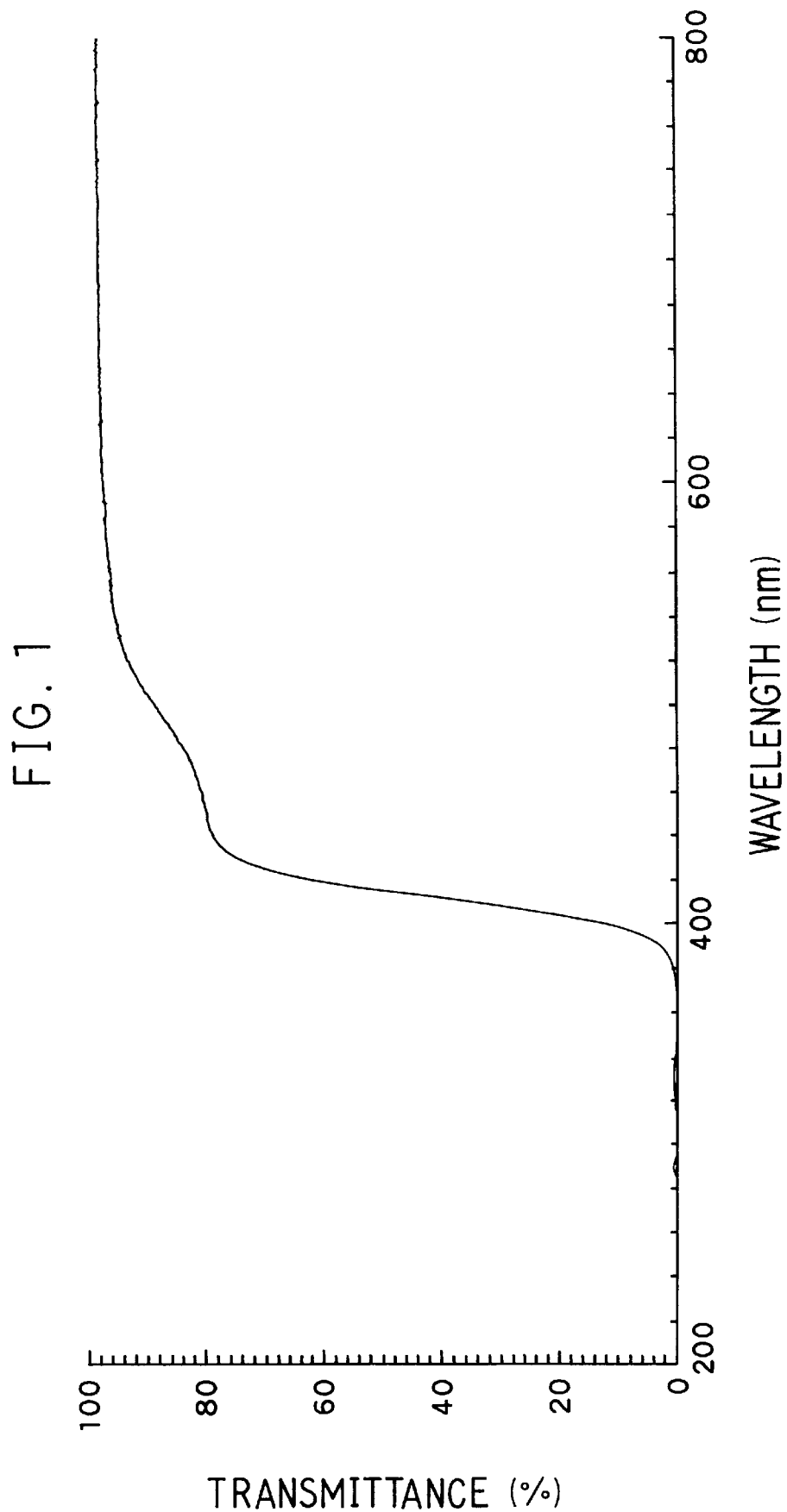

MATERIAL FOR A SOFT INTRAOCULAR LENS

BACKGROUND OF THE INVENTION

The present invention relates to a material for a soft intraocular lens. And more particularly it relates to a material for a soft intraocular lens, which is excellent in transparency and flexibility, can be inserted from a small incision, and has a high refractive index in spite of a high water content.

In order to make the size of the eye's injury small, which is cut in the operation of cataract by using an intraocular lens, it is desirable that an incision treated surgically is as small as possible. According to development of the phacoemulsificasion aspiration that the human's lens is broken by using an ultrasonic vibration and the fragment is sucked through a small cannula, human's lens can be removed through the incision not more than 2–3 mm.

However, since an intraocular lens usually has a diameter of about 6 mm, a large portion must be dissected in order to be inserted as it is. But various soft intraocular lenses have been recently developed, which are flexible and deformable, therefore, it becomes possible to be inserted through a small incision.

For instance, Japanese Unexamined Patent Publication No.292609/1992 discloses an intraocular lens obtained by co-polymerization of a monomer mixture, which contains at least two (meth)acrylate monomers containing an aromatic ring and a crosslinling monomer. Since the lens is certainly flexible, it can be deformed to the shape which is inserted through a small incision. But since an amount of (meth) acrylate monomers with an aromatic ring is comparatively large, it has a disadvantage of low mechanical strength. And it has another disadvantage that it is impossible to cut it by a mechanical process since the obtained polymer is soft.

Japanese Examined Patent Publication No.22565/1994 discloses the material for an intraocular lens of the copolymer, which comprises, as a main component, a hydroxyalkyl (meth)acrylate, (meth)acrylic acid ester and/or (meth)acrylic amide derivatives containing a ring structure such as a cycloalkyl group or a halogen atom except for a fluorine atom. The material for an intraocular lens can be inserted through a small incision, and it is excellent in a hydrophilic property and has a high refractive index. But a compatibility of the material component is low, therefore the transparency is desired to be improved more.

Japanese Unexamined Patent Publication No.73052/1997 discloses the material for a soft intraocular lens of the polymer, which comprises, as a main component, an acrylate containing predetermined amount of an aromatic ring and an alkyl acrylate containing a fluorine atom. The material for a soft intraocular lens has properties that a refractive index is comparatively high, recovery to the original shape is excellent, and an adhesiveness is low. But it is further desired that the polymer after polymerization is excellent in a mechanical processability, flexibility occurs by hydration after shaping, and the high refractive index is maintained at the hydration.

And Japanese Unexamined Patent Publication No.24052/1995 discloses the colored material for a soft intraocular lens as a soft intraocular lens for cyanopsia, which is obtained by adding a yellow colorant. It is usually possible to treat the soft material by extraction with an organic solvent or the like in order to remove the residual unpolymerized monomers therein. But the colorant of dispersion type disclosed in Japanese Unexamined Patent Publication No.24052/1995 is dissolved out in this extraction process, therefore the color of the lens forces to change.

It is an object of the present invention to provide a material for a soft intraocular lens which is excellent in transparency and flexibility, and can be inserted from a small incision. Further it has a high refractive index in spite of a high water content, and is excellent in mechanical processability into an intraocular lens shape in a xerogel state.

SUMMARY OF THE INVENTION

In accordance with the present invention, there is provided a material for a soft intraocular lens comprising a copolymer obtained by polymerizing the components for polymerization which contain (A)5–25% by weight of acrylate containing an aromatic ring represented by the general formula (I):

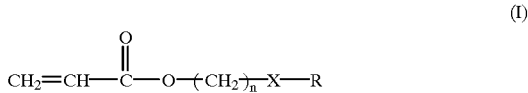

(I)

wherein R represents an aromatic ring of which hydrogen atom may be substituted by a substitutional group, X represents an oxygen atom or a direct bonding, and n represents an integer of 1 to 5,
(B)50–90% by weight of 2-hydroxyethyl (meth)acrylate, and
(C)5–45% by weight of a (meth)acrylate monomer except for the acrylate (A) containing an aromatic ring represented by the general formula (I) and 2-hydroxyethyl (meth) acrylate (B), wherein the coefficient of water absorption of its homopolymer is not more than 30% by weight.

BRIEF EXPLANATION OF THE DRAWINGS

FIG. 1 is a transmission spectrum measured between 360 to 800 nm by using the specimen of Example 6 of the present invention having 1 mm thickness.

DETAILED DESCRIPTION

The material for an intraocular lens of the present invention comprises, as mentioned above, a copolymer obtained by polymerizing the components for polymerization containing (A)5–25% by weight of acrylate containing an aromatic ring represented by the general formula (I) (hereinafter referred to "acrylate (A)")

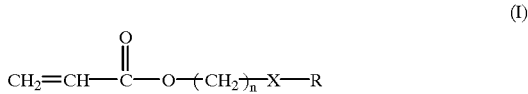

(I)

wherein R represents an aromatic ring of which hydrogen atom may be substituted by a substitutional group, X represents an oxygen atom or a direct bonding, and n represents an integer of 1 to 5,
(B)50–90% by weight of 2-hydroxyethyl (meth)acrylate (hereinafter referred to "2-HE(M)A (B)"), and (C)5–45% by weight of a (meth)acrylate monomer except for acrylate (A) and 2-HE(M)A (B) (hereinafter referred to as "(meth) acrylate monomer (C)"), wherein the coefficient of water absorption of its homopolymer is not more than 30% by weight.

And the material comprises a copolymer obtained by polymerizing the components for polymerization further containing a dye and/or a UV absorbant having a polymerizable substitutional group, which can be co-polymerized with (A) to (C).

One of the most important features is a preparation by using the particular amounts of particular acrylate (A), 2-HE(M)A (B) and (meth)acrylate monomer (C) having a particular coefficient of water absorption, and thereby there can be provided a material for a soft intraocular lens having excellent properties in mechanical processability and bio-compatibility in addition to transparency and flexibility, and which can be inserted from a small incision and has a high refractive index independent on the water content.

And by using a dye and a UV absorbant containing a polymerizable substitutional group, the possibility that the dye and the UV absorbant are dissolved out in an eye becomes extremely small, and the dye and the UV absorbant is prevented from dissolving out in case of extraction of the other unpolymerized components with an organic solvent.

The above-mentioned acrylate (A) is a component having an effect on improving a refractive index of the obtained material for a soft intraocular lens.

As the substitutional group represented by the general formula (I) of which hydrogen atom may be substituted by a substitutional group, examples are, for instance, an alkyl group containing 1 to 5 carbon atoms and a halogen atom such as a fluorine atom, a chlorine atom, a bromine atom or the like. The number of the substitutional groups may not be limited.

Examples of acrylate (A) are, for instance, phenyl acrylate, phenylethyl acrylate, benzyl acrylate (as examples that X is a direct bonding in the general formula(I)), 2-phenoxyethyl acrylate, 3-phenoxypropyl acrylate (as examples that X is an oxygen atom in the general formula (I)), pentabromophenyl acrylate (as examples that X is a direct bonding and an aromatic ring R has substitutional groups in the general formula(I)), and the like. These can be used solely or in a combination use of two or more thereof. Among those, phenoxyethyl acrylate is preferable from the view point that it can improve effectively a refractive index of the material for a soft intraocular lens and also a flexibility thereof.

The amount of acrylate (A) in components for polymerization is preferably not less than 5% by weight, more preferably not less than 7% by weight from the viewpoint of obtaining the material for a soft intraocular lens having an high refractive index. And it is preferably not more than 25% by weight, more preferably not more than 23% by weight, particularly not more than 15% by weight from the viewpoint of improving transparency of the material for a soft intraocular lens.

The above-mentioned 2-HE(M)A is a component having an effect on improving flexibility and bio-compatibility of the material for a soft intraocular lens.

The amount of 2-HE(M)A (B) in components for polymerization is preferably not less than 50% by weight, preferably not less than 55% by weight from the viewpoint of improving sufficiently flexibility of the material for a soft intraocular lens. And it is preferably not more than 90% by weight, more preferably not more than 85% by weight from the viewpoint of not decreasing a refractive index of the material for a soft intraocular lens.

The above-mentioned (meth)acrylate monomer (C) is a components having an effect on improving a refractive index of the obtained material for a soft intraocular lens furthermore.

The (meth)acrylate monomer (C) is the compound, wherein the coefficient of water absorption of homopolymer thereof is not more than 30% by weight. The coefficient is preferably not less than 0.5% by weight, more preferably not less than 0.8% by weight from the viewpoint of not decreasing flexibility of the obtained material for a soft intraocular lens. And it is preferably not more than 30% by weight, more preferably not more than 25% by weight, particularly not more than 10% by weight from the viewpoint of not decreasing the effect on improving a refractive index of the material for a soft intraocular lens.

In the present invention the coefficient of water absorption is defined as the following equation.

$$\text{Coefficient of Water Absorption}(\% \text{ by weight}) = ((W-W0)/W0) \times 100$$

wherein the value is calculated at 25° C. by using the specimen having 1 mm thickness at cutting, W represents a weight (g) of the specimen in equilibrium state of water, and W0 represeents a weight (g) of the specimen in a dry state.

Examples of a (meth)acrylate monomer (C) are, for instance, an alkyl (meth)acrylate containing a straight chain, a branched chain or cyclic chain such as methyl (meth) acrylate, ethyl (meth)acrylate, propyl (meth)acrylate, butyl (meth)acrylate, pentyl (meth)acrylate, hexyl meth)acrylate, heptyl (meth)acrylate, nonyl (meth)acrylate, stearyl meth) acrylate, octyl (meth)acrylate, decyl (meth)acrylate, lauryl (meth)acrylate, pentadecyl (meth)acrylate, 2-ethylhexyl (meth)acrylate, cyclopentyl (meth)acrylate, (meth)acrylate, cyclohexyl (meth)acrylate: an alkyl (meth)acrylate containing 1 to 5 carbon atoms of alkyl group: a hydroxyalkyl (meth)acrylate containing a straight chain, a branched chain or cyclic chain, except for 2-HE(M)A (B), and the like. These can be used solely or in a combination use of two or more thereof. Among those alkyl methacrylates containing 1 to 3 carbon atoms of alkyl group and hydroxyalkyl methacrylates containing 3 to 6 carbon atoms of hydroxyalkyl group are preferable from the viewpoint of the effect on improving an refractive index and not decreasing flexibility of the obtained material for a soft intraocular lens furthermore Among (meth)acrylate monomers (C), the coefficients of water absorption of homopolymer from typical monomers are shown below.

| | |
|---|---|
| methyl methacrylate | 1% by weight |
| ethyl methacrylate | 0.9% by weight |
| butyl methacrylate | 0.5% by weight |
| hydroxybutyl methacrylate | 8.6% by weight |

The amount of (meth)acrylate monomer (C) in the components for polymerization is preferably not less than 5% by weight, more preferably not less than 7% by weight from the viewpoint of not decreasing an effect on improving an refractive index of the material for a soft intraocular lens. And it is preferably not more than 45% by weight, more preferably not more than 35% by weight from the viewpoint of preventing flexibility of the material for a soft intraocular lens from decreasing due to the (meth)acrylate monomer (C).

Polymerization components employed in the present nvention to obtain a copolymer are the components containing acrylate (A), 2-HE(M)A (B) and (meth)acrylate monomer (C), but other polymerization monomers, which are co-polymerizable with acrylate (A), 2-HE(M)A (B) and acrylate monomer (C), may be suitably contained if necessary.

Examples of the polymerization monomers are, for instance, a hydrophilic monomer, a crosslinking monomer and the like except for a hydroxyalkyl (meth)acrylate shown as an example for 2-HE(M)A (B) and a (meth)acrylate monomer (C).

The above-mentioned hydrophilic monomer is a component having an effect on improving a hydrophilic property of the material for a soft intraocular lens.

Examples of the hydrophilic monomers are, for instance, N-vinyllactam such as N-vinylpyrolidone, N-vinylpiperidone, N-vinylcaprolactam, N,N-dialkyl (meth) acrylamide such as N,N-dimethyl (meth)acrylamide, N,N-diethyl (meth)acrylamide and N,N-dipropyl (meth) acrylamide, N,N-dialkylaminoalkyl (meth)acrylamide such as N,N-dimethylaminopropyl (meth)acrylamide and N,N-diethylaminopropyl (meth)acrylamide. These can be used solely or in a combination use of two or more thereof.

The amount of the hydrophilic monomer in the polymerization components is suitably selected in the range that hydrophilic property is sufficiently revealed and the object of the present invention is not obstructed.

The above-mentioned crosslinking monomer is a component having an effect on controlling flexibility of the obtained material for a soft intraocular lens, giving an excellent mechanical strength, improving apability of deformation recovery, and increasing co-polymerizable property with components for polymerization.

Examples of the crosslinking monomer are, for instance, butanediol di(meth)acrylate, ethylene glycol di(meth)acrylate, diethylene glycol di(meth)acrylate, triethylene glycol di(meth)acrylate, propylene glycol di(meth)acrylate, dipropylene glycol di(meth)acrylate, diallyl fumarate, allyl (meth)acrylate, vinyl (meth)acrylate, trimethylolpropane tri (meth)acrylate, methacryloyloxyethyl (meth)acrylate, divinylbenzene, diallyl phthalate, diallyl adipate, triallyl diisocyanate, a-methylene-N-vinylpyrrolidone, 4-vinylbenzyl(meth)aczylate, 3-vinylbenzyl (meth)acrylate, 2,2-bis((meth)acryloyloxyphenyl)hexafluoropropane, 2,2-bis((meth)acryloyloxyphenyl)propane, 1,4-bis(2-(meth)acryloyloxyhexafluoroisopropyl)benzene, 1,3-bis(2-(meth)acryloyloxyhexafluoroisopropyl)benzene, 1,2-bis(2-(meth)(acryloyloxyhexafluoroisopropyl)benzene, 1,4-bis(2-(meth)acryloyloxyisopropyl) benzene, 1,3-bis(2-(meth)acryloyloxyisopropyl)benzene, 1,2-bis(2-(meth)acryloyloxyisopropyl)benzene, and the like. These can be used solely or in a combination use of two or more thereof. Among those, ethylene glycol dimethacrylate and butanediol diacrylate are preferable from the viewpoint of the effects on controlling flexibility, giving an excellent mechanical strength, improving capability of deformation recovery, and increasing co-polymerizable property.

The amount of a crosslinking monomer in the components for polymerization is preferably not less than 0.05 part by weight, more preferably not less than 0.1 part by weight based on 100 parts by weight of the total components for polymerization except for the crosslinking onomer from the viewpoint of the effects on controlling flexibility of the obtained material for a soft intraocular lens, and improving capability of deformation recovery and co-polymerizable property. And it is preferably not more than 10 parts by weight, more preferably not more than 5 parts by weight from the viewpoint of not decreasing a refractive index and capability of deformation recovery.

The polymerizable UV absorbant is added in order to cut the harmful UV light. Since it contains a polymerizable substitutional group, the possibility that the UV absorbant is dissolved out in an eye becomes extremely small, and it is prevented from dissolving out in case of extraction of the other unpolymerized components with an organic solvent.

The amount of UV absorbant is preferably at least 0.01 part by weight, more preferably at least 0.05 part by weight from the viewpoint of the effect of cutting UV light. And it is preferably less than 5 parts by weight, more preferably less than 3 parts by weight from the viewpoint of obstruction of polymerization and transparency.

Examples of the polymerizable UV absorbent are, for instance, benzophenone compounds such as 2-hydroxy-4-methacryloyloxybenzophenone and 2-hydroxy-4-methacryloyloxyethyleneoxybenzophenone, benzotriazole compounds such as 2-(2'-hydroxy-5'-methacryloyloxyethyleneoxy-3'-tert-butyiphenyl)-5-methyl-benzotriazole, 2-(2'-hydroxy-5'-methacryloyloxyphenyl)benzotriazole, 5-cholro-2(3'-tert-butyl-2'-hydroxy-5'-methacryloyloxyethyleneoxyphenyl) benzotriazole, derivatives of salicylic acid, derivatives of hydroxyacetophenone and the like. These can be used solely or in a combination use of two or more thereof. Among those, the compounds represented by the following general formula (II) is preferably employed.

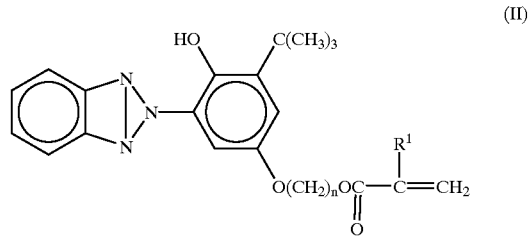

(II)

wherein $R^1$ represents H or $CH_3$, and n represents an integer of 2 or 3.

The polymerizable dye is added in order to correct cyanopsia, and decrease chronic retinal toxicity and glare. The amount of the polymerizable dye is preferably not less than 0.0001 part by weight, more preferably not less than 0.001 part by weight from the viewpoint of revealing the coloring effect. And it is preferably not more than 1 part by weight, more preferably not more than 0.5 part by weight from the viewpoint of excessively cutting the visible light.

As the polymerizable dye of the present invention, the dye represented by the following general formula (III) or (IV) is preferably employed.

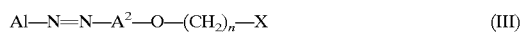

(III)

(IV)

Wherein $A^1$ represents an aryl group which may contain a substitutional group, $A^2$ represents an arylene group which may contain a substitutional group, X represents (meth) acryloyloxy, vinylphenyl, inylphenyloxy or vinylphenylalkyloxy containing 1 to 5 carbon atoms of an alkyl group, and n represents an integer of 1 to 5.

Examples of the polymerizable dye are, for instance, 2-phenylazo-4-methacryloyloxyethoxy-6-tert-butylphenol (BHP-PMA) represented by the formula (V), 1-phenylazo-3-methacryloyloxy-2-naphthol (BA-23M) represented by the formula (VI), 1-phenylazo-4-methacryloyloxynaphthalene(α-4BM) represented by the formula (VII), 2-(4-methyl)phenylazo-4-(meth) acryloyloxyethoxy-6-tert-butylphenol, 2-(3-methyl) phenylazo-4-(meth)acryloyloxyethoxy-6-tert-butylphenol, 2-(4-chloro)phenylazo-4-(meth)acryloyloxyethoxy-6-tert-butylphenol, 2-(2-chloro)phenylazo-4-(meth) acryloyloxyethoxy-6-tert-butylphenol, 2-phenylazo-4-(meth):acyloyloxypropox6-tert-butylphenol, 2-(4-methyl) phenylazo-4-(meth)acryloyloxypropoxy-6-tert-butylphenol, 2-(3-methyl)phenylazo-4-(meth)acryloyloxypropoxy-6-tertbutylphenol, 2-(4-chloro)phenylazo-4-(meth)acryloyloxypropoxy-6-tert-butylphenol, 2-(2-chloro)phenylazo-4-(meth)acryloyloxypropoxy-6-tert-butylphenol, 2-2-chloro)phenylazo-4-(meth)acryloyloxy propoxy-6-tert-butylphenol, 2 -phenylazo-4-(meth)acryloyloxyethoxy-6-methylphenol, 2-phenylazo-4-(meth)acryloyloxyethoxy-6-(2-methyl)butylphenol, 2-(1-naphthylazo)-4-(meth)acryloyloxyethoxy-6-tert-butylphenol, 2-(4-methyl-1-naphthylazo)-4-(meth)acryloyloxyethoxy-6-tert-butylphenol, 2-(4-chloro-1-naphthylazo)-4-(meth)acryloyloxyethoxy-6-tert-butylphenol, 2-(1 -naphthylazo)-4-(meth)acryloyloxypropoxy-6-tert-butylphenol, 2-(1-naphthylazo)-4-(meth)acryloyloxyethoxy-6-methylphenol, 2-phenylazo-4-(4-vinyl)phenoxyethoxy-6-tert-butylphenol, 1-phenylazo-4-(meth)acryloyloxyethoxy-2-naphthol, 2-phenylazo-4-(4-vinyl)benzyloxy-6-tert-butylphenol, 2-phenylazo-4-(4-vinyl)benzyl-6-tert-butylphenol and the like. In the above-mentioned examples, the word (meth) acryloyloxy represents the two compounds of acryloyloxy and methacryloyloxy.

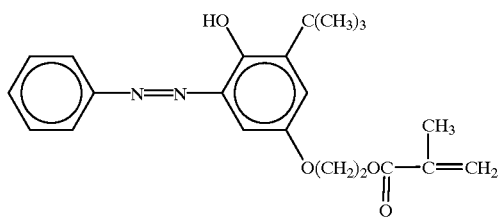

(V)

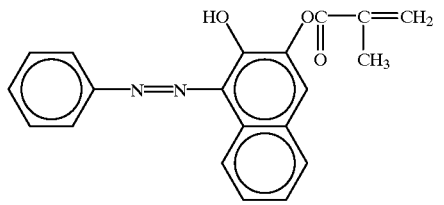

(VI)

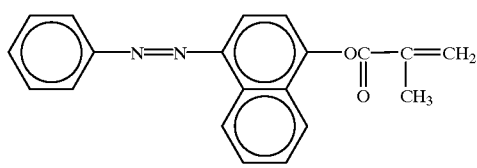

(VII)

Among those, 2-phenylazo-4-methacryloyloxyethoxy-6-tert-butylphenol (BHP-PMA), 1-phenylazo-3-methacryloyloxy-2-naphthol (BA-23M) and 1 -phenylazo-4-methacryloyloxynaphthalene (α-4BM) are preferable.

After a dye and a UV absorbant having a polymerizable sbstitutional group which is polymerizable with (A) to (C) are mixed with the components for polymerization containing acrylate (A), 2-HE(M)A (B), (meth)acrylate monomer (C) and the other optional components for polymerization, they are polymerized by adding a radical polymerization initiator in a conventional manner to obtain a material for a soft intraocular lens of the present invention.

As the above-mentioned conventional method, for example, the polymerization is started by heating gradually from room temperature to 130° C., or irradiating electromagnetic radiation such as microwave, ultraviolet light or radiation (γray) after a radical polymerization initiator is added to components for polymerization. In case of heating, the components may be heated stepwise. And the polymerization method may be the bulk polymerization, the solution polymerization using a solvent or the like.

Examples of the above-mentioned radical polymerization initiator are, for instance, azobisisobutyronitorile, azobisdimethylvaleronitrile, benzoyl peroxide, tert-butyl hydroperoxide, qumene hydroperoxide and the like. These can be used solely or in a combination use of two or more thereof.

In case of the polymerization by using a light and the like, a photopolymerization initiator and an intensifier may be preferably added.

Examples of the above-mentioned photopolymerization initiator are, for instance, photopolymerization initiators of benzoin compounds such as methyl orthobenzoyl benzoate, methyl benzoyl formate, benzoin methyl ether, benzoin ethyl ether, benzoin isopropyl ether, benzoin isobutyl ether and benzoin n-butyl ether, photopolymerization initiators of phenone compounds such as 2-hydroxy-2-methyl-1-phenylpropane-1-one, p-isopropyl-α-hydroxyisobutylphenone, p-tert-butyltrichloroacetophenone, 2,2-dimethoxy-2-phenylacetophenone, α,α-dichloro-4-phenoxyacetophenone, and N,N-tetraethyl-4,4-diaminobenzophenone, 1-hydroxycyclohexylphenylketone, 1-phenyl-1,2-propanedione-2-(o-ethoxycarbonyl)oxime, photopolymerization initiators of thioxanthone such as 2-chlorothioxanthone and 2-methylthioxanthone, dibenzosuberone, 2-ethylanthraquinone, benzophenone acrylate, benzophenone, benzil and the like.

The amount of the above-mentioned polymerization initiator and the above-mentioned intensifier is preferably not less than 0.002 part by weight, more preferably 0.01 part by weight based on 100 parts of the total components for polymerization from the viewpoint of promotion of the moderate polymerization rate. And it is preferably not more than 10 parts by weight, more preferably not more than 2 parts based on 100 parts of the total components for polymerization from the viewpoint of avoiding forming a void in the material for a soft intraocular lens.

In case of shaping the material for a soft intraocular lens of the present invention into a soft intraocular lens, conventional shaping methods used by the skilled in the art can be employed. Example of the shaping methods are, for instance, a mechanical process method, a molding method and the like. The mechanical process method is that after the components for polymerization is polymerized in a prescribed mold or container to obtain the material (copolymer) having a stick, block or plate-like shape, the material is processed into the desired shape by mechanical processing such as cutting or polishing. On the other hand, the molding method is that the above-mentioned components for polymerization are polymerized in the mold corresponding to the shape of the desired intraocular lens to obtain the copolymer, and the obtained lens can be processed mechanically on an occasion as a finishing process. As the above-mentioned mold or container, in which the components for polymerization are polymerized, the molds or containers made of glass or plastic such as polyethylene or polypropylene can be employed.

Besides these methods, the following method is applicable that the monomers, which give hardness, are immersed into the material for a soft intraocular lens and the monomers are polymerized to obtain the shapes (a soft intraocular lens) made of the material for a soft intraocular lens by mechanically processing and removing the hard polymer from the shaping processed into the desired shape (described in Japanese Unexamined Patent Publication Nos.278041/1987 and 11854/1989).

In case of obtaining the soft intraocular lens from the material for a soft intraocular lens of the present invention, a supporting portion of lens may be prepared separately, and may be attached to the lens by making a hole in the lens and passing the shaped portion into the hole. Or the supporting portion of lens may be prepared simultaneously by shaping with a lens.

Since the obtained material for an intraocular lens of the present invention is the material obtained by using a particular amount of acrylate monomer, it shows mechanical processability and bio-compatibility in addition to an excellent transparency and flexibility and it can be inserted from the small incision. And it can provide a soft intraocular lens having a high refractive index in spite of a high water content.

EDMA: ethylene glycol dimethacrylate
BDDA: butanediol diacrylate
(ultraviolet light absorbent)
Sb-7010MA: 2-[2'hydroxy-5'-(2"-methacryloyloxyethoxy)-3'-tert-butylphenyl]-5-metyl-2H-benzotriazole
(dye)
BHP-PMA: 2-phenylazo-4-methacryloyloxyethoxy-6-tert-butylphenol
(other monomer)
POEMA: 2-phenoxyethyl methacrylate And an amount of crosslinking monomer shown in Table 1 is based on 100 parts of the total amount of acrylate (A), 2-HE(M)A (B), (meth)acrylate monomer (C) and the other monomers.

TABLE 1

| | Polymerization Component (parts) | | | | | | |
|---|---|---|---|---|---|---|---|
| | Acrylate (A) | 2-HE(M)A (B) (HEMA) | (Meth)acrylate monomer (C) | Crosslinking monomer | Other monomer | Dye | UV Absorbant |
| Ex. 1 | POEA (10) | (80) | MMA (10) | EDMA (0.2) | — | | |
| Ex. 2 | POEA (10) | (80) | EMA (10) | EDMA (0.2) | — | | |
| Ex. 3 | POEA (10) | (70) | HBMA (20) | BDDA (2) | — | | |
| Ex. 4 | POEA (20) | (70) | HBMA (10) | BDDA (2) | — | | |
| Ex. 5 | POEA (20) | (50) | HBMA (30) | BDDA (2) | — | | |
| Ex. 6 | POEA (10) | (70) | HBMA (20) | BDDA (2) | — | BHP-PMA (0.011) | Sb-7010MA (0.22) |
| Com. Ex. 1 | POEA (10) | (90) | — | EDMA (0.2) | — | | |
| Com. Ex. 2 | POEA (30) | (70) | — | BDDA (2) | — | | |
| Com. Ex. 3 | POEA (40) | (60) | — | BDDA (2) | — | | |
| Com. Ex. 4 | POEA (40) | (50) | HBMA (10) | BDDA (2) | — | | |
| Com. Ex. 5 | — | (60) | — | EDMA (0.2) | PEOMA (40) | | |

EXAMPLES

The present invention is further explained in details based on the Examples concretely, but is not limited thereto.

Examples 1 to 5 and Comparative Examples 1 to 5

Components for polymerization shown in table 1 and 0.1 part of 2,2-azobis(2,4-dimethylvaleronitrile) as a polymerization initiator based on 100 parts of total components for polymerization were mixed. After the mixture was poured into a glass tube, the tube was put in a constant-temperature water bath to polymerize it by maintaining at 35° C. for 40 hours and heating at 50° C. for 8 hours.

Subsequently the above-mentioned tube was transferred to a circulating drier, and was heated to 120° C. from 50° C. at a rate of 10° C. per 1.5 hours. It was maintained at 130° C. for 3 hours and allowed to stand to cool to room temperature to obtain a cylindrical copolymer (a material for a soft intraocular lens).

Abbreviations in tables indicate the followings:
(acrylate (A))
POEA: 2-phenoxyethyl acrylate
(2-HE(M)A (B))
HEMA: 2-hydroxyethyl methacrylate
((meth)acrylate monomer (C))
MMA: methyl methacrylate
EMA: ethyl methacrylate
HBMA: 2-hydroxybutyl methacrylate
(crosslinking monomer)

Subsequently, specimens having a pre-determined thickness were prepared by cutting the obtained cylindrical copolymer. After unpolymerized monomers were removed in isopropanol, isopropanol was evaporated by heating. By using the specimens allowed to stand in a physiological saline to be in equilibrium of imbibition, as the physical properties of a material for a soft intraocular lens, transparency, mechanical processability, flexibility, water content and a refractive index were examined in accordance with the following methods. The results are shown in Table 1.

(A) Transparency

Appearance (transparency) of specimens having 1 mm thickness was visually observed by using the projector (V-12B, made by NIKON CORPORATION) to evaluate by the following criterion for evaluation.
(Criterion for Evaluation)
⊚: Transparent.
○: Slightly cloudy, but no problems practically in transparency.
Δ: Cloudy was observed.
×: Cloudy and opaque.

(B) Mechanical Processability

Specimens having 1 mm thickness were prepared by cutting the obtained cylindrical copolymer, and the surface appearance was visually observed to evaluate by the following criterion for evaluation.
(Criterion for Evaluation)
○: Brilliant on surface.
Δ: Not brilliant on surface
×: Mechanical process was impossible.

(C) Flexibility

Specimens having 1 mm thickness were folded up by using tweezers and a feel of the folding and a recovery thereof was evaluated by the following criterion for evaluation.

(Criterion for Evaluation)

⊚: Specimens can be very easily folded up without an excess force, and slight time is required until recovery to the original shape.

○: Specimens can be easily folded up without an excess force, and the shape is recovered to the original shape in a comparative short time.

Δ: Specimens can be folded up with an excess force, and the shape is difficult to be recovered to the original shape.

×: Specimens can not be folded up.

(D) Water content

Water content of the specimen having 0.2 mm thickness at 25° C. was calculated by the following equation.

$$\text{Water Content (\% by weight)} = ((W - W0)/w) \times 100$$

wherein W represents a weight (g) of the specimen in equilibrium state of moisture, and W0 represents a weight (g) of the specimen in dry state.

(E) Refractive index

In accordance with Japanese Industrial Standards (JIS) K-7105 the refractive index (n25D) (no unit) of the specimen having 1.0 mm thickness was measured by using Abbe's refractometer (1-T, made by ATAGO CORPORATION) at the condition of 25° C. and 50% humidity. The specimens of Comparative Examples 2 to 4 could not be measured, since they were opaque.

(F) Transmission Spectrum (only Example 6 was Measured)

Transmission spectrum at 190–800 nm of the specimens having 0.5 mm thickness was measured by using a spectrophotometer (UV-3100, made by Shimadzu Corporation). The result is shown in FIG. 1.

TABLE 2

Properties of Specimen (Material for a soft intraocular lens)

| | Transparency | Mechanical processability | Flexibility | Moisture content (% by weight) | Refractive index (–) |
|---|---|---|---|---|---|
| Ex. 1 | ⊚ | ○ | ⊚ | 18.0 | 1.472 |
| Ex. 2 | ⊚ | ○ | ⊚ | 19.0 | 1.473 |
| Ex. 3 | ⊚ | ○ | ⊚ | 20.0 | 1.478 |
| Ex. 4 | ○ | ○ | ⊚ | 18.0 | 1.485 |
| Ex. 5 | ○ | ○ | ⊚ | 13.0 | 1.494 |
| Com. Ex. 1 | ⊚ | ○ | ⊚ | 29.0 | 1.458 |
| Com. Ex. 2 | Δ | ○ | ⊚ | 16.0 | (impossible) |
| Com. Ex. 3 | × | ○ | ⊚ | 12.0 | (impossible) |
| Com. Ex. 4 | × | ○ | ⊚ | 10.0 | (impossible) |
| Com. Ex. 5 | ⊚ | ○ | × | 8.8 | (not measured) |

As is clear from the results shown in Table 2, it can be seen that the materials for a soft intraocular lens obtained in Example 1 to 5 are excellent in transparency, mechanical processability, flexibility and moreover have a high refractive index of not less than 1.47 in spite of a high water content.

On the contrary, it can be seen that the materials for a soft intraocular lens obtained in Comparative Example 1 to 5 are poor in flexibility (Comparative Example 5), transparency (Comparative Example 2, 3 and 4), have a low refractive index (Comparative Example 1), and all of them do not have excellent properties as the material obtained in Example 1 to 5. The plate was colored to yellow, and it could not be decolored by the extraction treatment of an organic solvent.

The soft intraocular lens material of the present invention is excellent in not only transparency, flexibility, but also mechanical processability, bio-compatibility, and it can be inserted from the small incision. And it can provide a soft intraocular lens having exvellent properties such as having a high refractive index independent on the water content.

What is claimed is:

1. A material for a soft intraocular lens comprising a copolymer obtained by polymerizing components for polymerization, which contain (A) 5–25% by weight of acrylate containing an aromatic ring represented by the general formula (I):

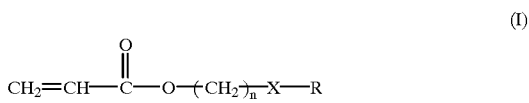

(I)

wherein R represents an aromatic ring of which hydrogen atom may be substituted by a substitutional group, X represents an oxygen atom or a direct bonding, and n represents an integer of 1 to 5, (B) 50–90% by weight of 2-hydroxyethyl (meth)acrylate, and (C) 5–45% by weight of a (meth)acrylate monomer having the coefficient of water absorption of the homopolymer thereof of not more than 30% by weight, with the proviso that monomer (C) is not a (meth)acrylate monomer corresponding with either monomer (A) or monomer (B).

2. The material for a soft intraocular lens of claim 1, wherein (C) the (meth)acrylate monomer is at least one monomer selected from the group consisting of an alkyl methacrylate containing 1 to 3 carbon atoms of an alkyl group and a hydroxyalkyl methacrylate containing 3 to 6 carbon atoms of a hydroxyalkyl group.

3. The material for a soft intraocular lens of claim 2, wherein the material contains a polymerizable ultraviolet absorbant and/or a polymerizable dye.

4. The material for a soft intraocular lens of claim 3, wherein the polymerizable ultraviolet absorbant is the compound represented by the following general formula II:

4-methacryloyloxynaphthalene represented by the formula (VII).

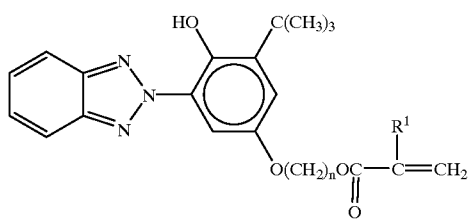

(II)

wherein $R^1$ represents H or $CH_3$, and n represents an integer of 2 or 3.

5. The material for a soft intraocular lens of claim 3, wherein the polymerizable dye is the compound represented by the following general formula (III) or (IV):

$$A^1-N=N-A^2-O-(CH_2)_n-X \quad (III)$$

$$A^1-N=N-A^2-X \quad (IV)$$

wherein $A^1$ represents an aryl group which may contain a substitutional group, $A^2$ represents an arylene group which may contain a substitutional group, X represents (meth)acryloyloxy, vinylphenyl, vinylphenyloxy or vinylphenylalkyloxy containing 1 to 5 carbon atoms of an alkyl group, and n represents an integer of 1 to 5.

6. The material for a soft intraocular lens of claim 3, wherein the polymerizable dye is the compound selected from the group consisting of 2-phenylazo-4-methacryloyloxyethoxy-6-tert-butylphenol represented by the formula (V), 1-phenylazo-3-methacryloyloxy-2-naphthol represented by the formula (VI), and 1-phenylazo-

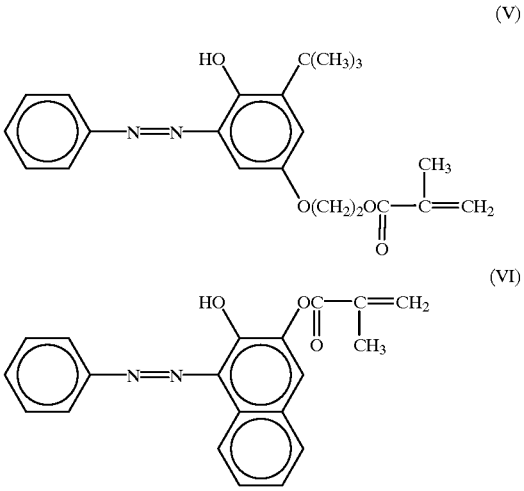

* * * * *